(12) United States Patent
Kermani (10) Patent No.: US 12,324,792 B2
(45) Date of Patent: Jun. 10, 2025

(54) METHODS FOR MAKING AND USING PHARMACEUTICAL COMPOSITIONS FOR IONTOPHORESIS

(71) Applicants: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

(72) Inventor: Mahyar Z. Kermani, San Ramon, CA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 888 days.

(21) Appl. No.: 17/520,053

(22) Filed: Nov. 5, 2021

(65) Prior Publication Data

US 2022/0202749 A1 Jun. 30, 2022

Related U.S. Application Data

(60) Provisional application No. 63/131,099, filed on Dec. 28, 2020.

(51) Int. Cl.
*A61K 31/167* (2006.01)
*A61K 31/137* (2006.01)
*A61N 1/30* (2006.01)

(52) U.S. Cl.
CPC .......... *A61K 31/167* (2013.01); *A61K 31/137* (2013.01); *A61N 1/30* (2013.01)

(58) Field of Classification Search
CPC ....... A61K 31/167; A61K 31/137; A61N 1/30
See application file for complete search history.

(56) References Cited

U.S. PATENT DOCUMENTS

| 5,503,632 A | 4/1996 | Haak |
| 5,540,669 A * | 7/1996 | Sage, Jr. ................ A61N 1/044 |
| | | 604/20 |
| 5,730,714 A * | 3/1998 | Guy ....................... A61N 1/303 |
| | | 604/20 |

(Continued)

FOREIGN PATENT DOCUMENTS

| JP | 2007244700 A | 9/2007 |
| WO | 199820869 A2 | 5/1998 |
| WO | 200151120 A1 | 7/2001 |

*Primary Examiner* — Dung T Ulsh
(74) *Attorney, Agent, or Firm* — Dickinson Wright PLLC (57) ABSTRACT

Methods of making and using pharmaceutical compositions for iontophoresis that include selecting an isotonic pharmaceutical composition that has ions of active and non-active ingredients and reducing/removing the ions of the non-active ingredients from the pharmaceutical composition to produce a revised pharmaceutical composition. The revised pharmaceutical composition is thereafter utilized for iontophoresis in an iontophoresis system. During the step of performing iontophoresis with the revised pharmaceutical composition for a pre-determined dosage, ramp-up period, maximum current, overall time, etc., can be reduced, as compared to performing iontophoresis with the isotonic pharmaceutical composition to provide the pre-determined dosage.

29 Claims, 6 Drawing Sheets

(56) References Cited

U.S. PATENT DOCUMENTS

| | | | |
|---|---|---|---|
| 5,788,666 A | 8/1998 | Atanasoska | |
| 5,985,316 A * | 11/1999 | Gyory | A61N 1/30 424/449 |
| 6,635,045 B2 | 10/2003 | Keusch et al. | |
| 2005/0074810 A1 * | 4/2005 | Guy | A61N 1/30 435/7.1 |
| 2007/0078372 A1 | 4/2007 | Reddy et al. | |
| 2007/0093743 A1 | 4/2007 | Keusch et al. | |
| 2008/0058756 A1 * | 3/2008 | Smith | A61N 1/044 604/20 |

* cited by examiner

METHODS FOR MAKING AND USING PHARMACEUTICAL COMPOSITIONS FOR IONTOPHORESIS

CROSS-REFERENCE TO RELATED APPLICATIONS

This application claims the benefit of U.S. Provisional Application Ser. No. 63/131,099 filed Dec. 28, 2020 titled "Methods for Making and Using Pharmaceutical Compositions for Iontophoresis." The provisional application is incorporated by reference herein as if reproduced in full below.

TECHNICAL FIELD

Example embodiments relate to iontophoretic drug delivery methods and systems, and more particularly to methods of making and using pharmaceutical compositions for iontophoresis.

BACKGROUND

Iontophoresis is a method for delivering a drug across a biological membrane, such as the skin or, in the case of certain ear surgery procedures, the tympanic membrane. By applying low-level electrical current to a similarly charged drug solution, iontophoresis repels ions of the drug, thus transporting them across the skin or other membrane. Molecules are transported across the stratum corneum by electrophoresis and electroosmosis and the electric field can also increase the permeability of the skin. These phenomena, directly and indirectly, constitute active transport of matter due to an applied electric current.

SUMMARY

The present invention relates to methods of making and using pharmaceutical compositions for iontophoresis.

In general, in one aspect, is a method that includes selecting an isotonic pharmaceutical composition. The isotonic pharmaceutical composition includes charged ions of one or more active ingredients. The isotonic pharmaceutical composition further includes competing ions of one or more non-active ingredients. The isotonic pharmaceutical composition is operable for being used in an iontophoresis system to perform iontophoresis. The method further includes removing at least 50% molar concentration of the competing ions from the isotonic pharmaceutical composition to produce a revised pharmaceutical composition. The method further includes utilizing the revised pharmaceutical composition in the iontophoresis system to perform iontophoresis.

Implementations can include one or more of the following features:

The charged ions of the one or more active ingredients can be positively charged ions.

The charged ions of the one or more active ingredients can be negatively charged ions.

The one or more active ingredients can include (i) lidocaine, (ii) epinephrine, or (iii) a combination of both. The competing ions of the one or more non-active ingredients can include (i) sodium ions, (ii) chlorine ions, or (iii) a combination of both.

At least 75% molar concentration of the competing ions of the one or more non-active ingredients can be removed from the isotonic pharmaceutical composition to produce the revised pharmaceutical composition.

At least 90% molar concentration of the competing ions of the one or more non-active ingredients can be removed from the isotonic pharmaceutical composition to produce the revised pharmaceutical composition.

At least 99% molar concentration of the competing ions of the one or more non-active ingredients can be removed from the isotonic pharmaceutical composition to produce the revised pharmaceutical composition.

All of the competing ions can be removed from the isotonic pharmaceutical composition to produce the revised pharmaceutical composition.

The isotonic pharmaceutical composition can have a standard measured pre-determined dosage characteristic. The revised pharmaceutical composition can have a revised measured pre-determined dosage characteristic. The standard measured pre-determined dosage characteristic can be a standard measured pre-determined dosage obtained when utilizing the isotonic pharmaceutical composition in a Franz cell performing iontophoresis using a standard profile of (i) a standard ramp-up from 0.1 mA to 0.8 mA for 3.5 minutes, (ii) a standard steady state at 0.8 mA for 5.5 minutes, and (iii) a standard ramp-down from 0.8 mA to 0.1 mA for 1 minute. The revised measured pre-determined dosage characteristic can be a revised measured pre-determined dosage obtained when utilizing the revised pharmaceutical composition in the Franz cell performing iontophoresis using a second profile of (i) a second ramp-up from 0.1 mA to 0.7 mA for 3 minutes, (ii) a second steady state at 0.7 mA for 3.75 minutes, and (iii) a second ramp-down from 0.7 mA to 0.1 mA for 50 seconds. The revised measured pre-determined dosage can be equal or greater than the standard measured pre-determined dosage.

The one or more active ingredients can include (i) lidocaine, (ii) epinephrine, or (iii) a combination of both. The competing ions of the one or more non-active ingredients can include (i) sodium ions, (ii) chlorine ions, or (iii) a combination of both.

At least 75% molar concentration of the competing ions of the one or more non-active ingredients can be removed from the isotonic pharmaceutical composition to produce the revised pharmaceutical composition.

At least 90% molar concentration of the competing ions of the one or more non-active ingredients can be removed from the isotonic pharmaceutical composition to produce the revised pharmaceutical composition.

At least 99% molar concentration of the competing ions of the one or more non-active ingredients can be removed from the isotonic pharmaceutical composition to produce the revised pharmaceutical composition.

All of the competing ions of the one or more non-active ingredients can be removed from the isotonic pharmaceutical composition to produce the revised pharmaceutical composition.

At least 75% molar concentration of the competing ions of the one or more non-active ingredients can be removed from the isotonic pharmaceutical composition to produce the revised pharmaceutical composition. The isotonic pharmaceutical composition can have a standard measured pre-determined dosage characteristic. The revised pharmaceutical composition can have a revised measured pre-determined dosage characteristic. The standard measured pre-determined dosage characteristic can be a standard measured pre-determined dosage obtained when utilizing the isotonic pharmaceutical composition in a Franz cell performing iontophoresis using a standard profile of (i) a standard ramp-up from 0.1 mA to 0.8 mA for 3.5 minutes, (ii) a standard steady state at 0.8 mA for 5.5 minutes, and (iii) a standard ramp-down from 0.8 mA to 0.1 mA for 1 minute. The revised measured pre-determined dosage characteristic can be a revised measured pre-determined dosage obtained when utilizing the revised pharmaceutical composition in the Franz cell performing iontophoresis using a second profile of (i) a second ramp-up from 0.1 mA to 0.6 mA for 2.5 minutes, (ii) a second steady state at 0.6 mA for 2 minutes, and (iii) a second ramp-down from 0.6 mA to 0.1 mA for 40 seconds. The revised measured pre-determined dosage can be equal or greater than the standard measured pre-determined dosage.

The one or more active ingredients can include (i) lidocaine, (ii) epinephrine, or (iii) a combination of both. The competing ions of the non-active ingredient can include (i) sodium ions, (ii) chlorine ions, or (iii) a combination of both.

At least 90% molar concentration of the competing ions of the one or more non-active ingredients can be removed from the isotonic pharmaceutical composition to produce the revised pharmaceutical composition.

The one or more active ingredients can include (i) lidocaine, (ii) epinephrine, or (iii) a combination of both. The competing ions of the one or more non-active ingredients can include (i) sodium ions, (ii) chlorine ions, or (iii) a combination of both.

At least 99% molar concentration of the competing ions of the one or more non-active ingredients can be removed from the isotonic pharmaceutical composition to produce the revised pharmaceutical composition.

All of the competing ions of the one or more non-active ingredients can be removed from the isotonic pharmaceutical composition to produce the revised pharmaceutical composition.

At least 75% molar concentration of the competing ions of the one or more non-active ingredients can be removed from the isotonic pharmaceutical composition to produce the revised pharmaceutical composition. The isotonic pharmaceutical composition can have a standard measured pre-determined dosage characteristic. The revised pharmaceutical composition can have a revised measured pre-determined dosage characteristic. The standard measured pre-determined dosage characteristic can be a standard measured pre-determined dosage obtained when utilizing the isotonic pharmaceutical composition in a Franz cell performing iontophoresis using a standard profile of (i) a standard ramp-up from 0.1 mA to 0.8 mA for 3.5 minutes, (ii) a standard steady state at 0.8 mA for 5.5 minutes, and (iii) a standard ramp-down from 0.8 mA to 0.1 mA for 1 minute. The revised measured pre-determined dosage characteristic can be a revised measured pre-determined dosage obtained when utilizing the revised pharmaceutical composition in the Franz cell performing iontophoresis using a second profile of (i) a second ramp-up from 0.1 mA to 0.6 mA for 1.25 minutes, (ii) a second steady state at 0.6 mA for 2.75 minutes, and (iii) a second ramp-down from 0.6 mA to 0.1 mA for 30 seconds. The revised measured pre-determined dosage can be equal or greater than the standard measured pre-determined dosage.

The one or more active ingredients can include (i) lidocaine, (ii) epinephrine, or (iii) a combination of both. The competing ions of the one or more non-active ingredients can include (i) sodium ions, (ii) chlorine ions, or a combination of both.

At least 90% molar concentration of the competing ions can be removed from the isotonic pharmaceutical composition to produce the revised pharmaceutical composition.

The one or more active ingredients can include (i) lidocaine, (ii) epinephrine, or (iii) a combination of both. The competing ions of the one or more non-active ingredients can include (i) sodium ions, (ii) chlorine ions, or (iii) a combination of both.

At least 99% molar concentration of the competing ions can be removed from the isotonic pharmaceutical composition to produce the revised pharmaceutical composition.

All of the competing ions of the non-active ingredients can be removed from the isotonic pharmaceutical composition to produce the revised pharmaceutical composition.

During the step of performing iontophoresis with the revised pharmaceutical composition for a pre-determined dosage, overall time and maximum current can be reduced, as compared to performing iontophoresis with the isotonic pharmaceutical composition to provide the pre-determined dosage.

The charged ions of the one or more active ingredients can be positively charged ions.

The charged ions of the one or more active ingredients can be negatively charged ions.

The one or more active ingredients can include (i) lidocaine, (ii) epinephrine, or (iii) a combination of both. The competing ions of the one or more non-active ingredients can include (i) sodium ions, (ii) chlorine ions, or (iii) a combination of both.

At least 75% molar concentration of the competing ions of the one or more non-active ingredients can be removed from the isotonic pharmaceutical composition to produce the revised pharmaceutical composition.

At least 90% molar concentration of the competing ions of the one or more non-active ingredients can be removed from the isotonic pharmaceutical composition to produce the revised pharmaceutical composition.

At least 99% molar concentration of the competing ions of the one or more non-active ingredients can be removed from the isotonic pharmaceutical composition to produce the revised pharmaceutical composition.

All of the competing ions of the one or more non-active ingredients can be removed from the isotonic pharmaceutical composition to produce the revised pharmaceutical composition.

DETAILED DESCRIPTION

Example embodiments are directed to iontophoretic drug delivery methods and systems, and more particularly directed to methods of making and using pharmaceutical compositions for iontophoresis. The method first involves selecting a pharmaceutical composition that is an isotonic drug (an "isotonic pharmaceutical composition") in which the active ingredients are ions in the solution having the same directional charge, i.e., the active ingredients are all positively charged ions or all negatively charged ions. Since the active ingredients in the isotonic pharmaceutical composition are charged ions, a pre-determined dosage of the active ingredient or ingredients can be delivered utilizing iontophoresis.

Therapeutically, electromotive drug administration (EMDA) delivers a medicine or other chemical through the skin. It is different from dermal patches, which do not rely on an electric field. Iontophoresis drives a charged substance, usually a medication or bioactive agent, transdermally by repulsive electromotive force, through the skin. A small electric current is applied to an iontophoretic chamber placed on the skin, containing a charged active agent and its solvent vehicle. Another chamber or a skin electrode carries the return current. One or two chambers are filled with a solution containing an active ingredient and its solvent vehicle. The positively charged chamber, called the anode, will repel a positively-charged chemical species, whereas the negatively charged chamber, called the cathode, will repel a negatively-charged species into the skin.

For example, in ear procedures, attempts have been made in the past to use iontophoresis to anesthetize (or "numb") a tympanic membrane before placing an ear tube across it to treat chronic ear infections. For tympanic membrane iontophoresis, a drug solution is placed in an ear canal and current is applied to the solution, thus transporting the anesthetizing drug across the tympanic membrane.

Figure 1:
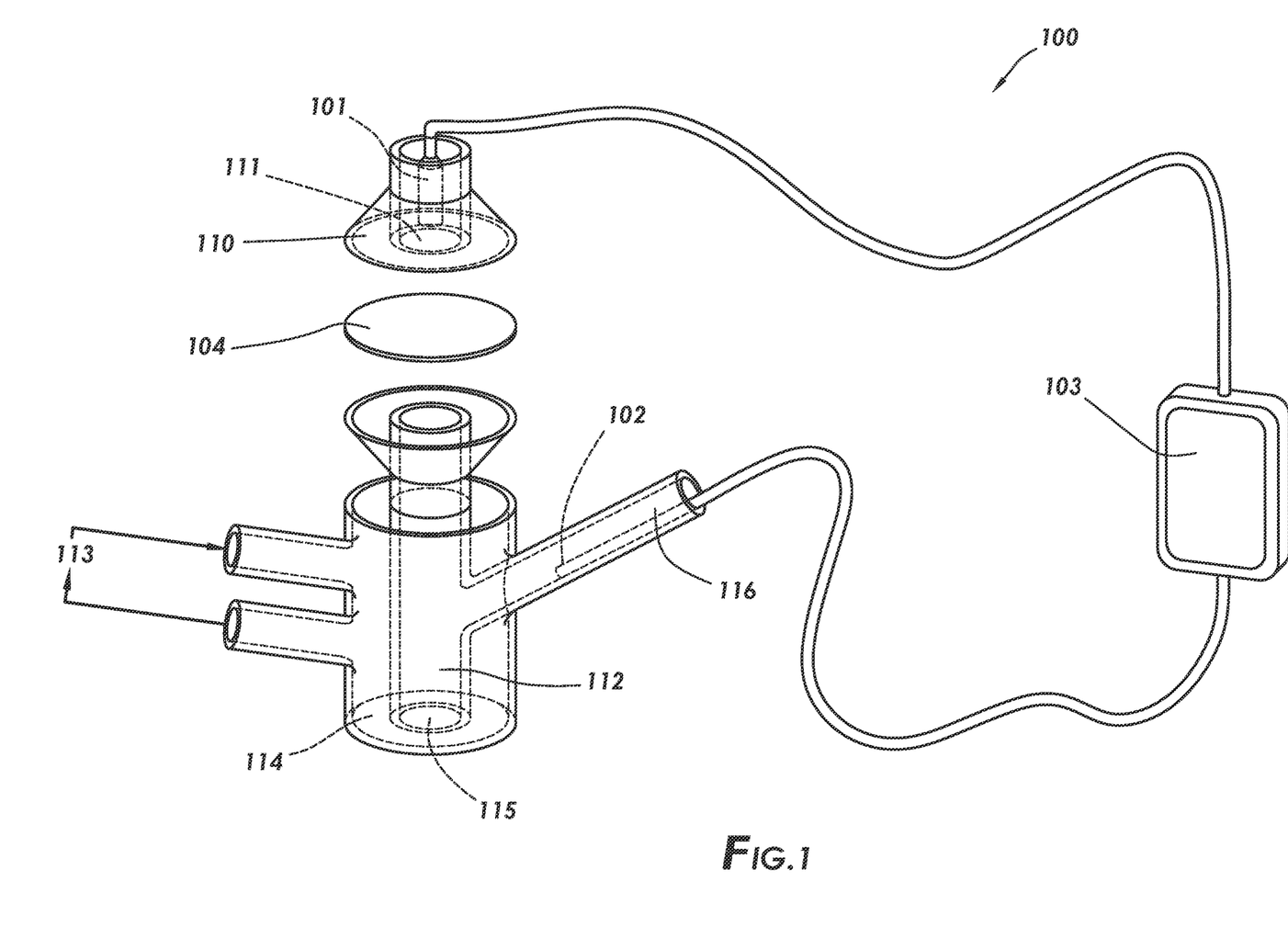
FIG. 1 is an exploded view of an illustration of an iontophoresis system in a Franz cell to simulate drug delivery into a body.

FIG. 1 is an exploded view of an illustration of an iontophoresis system 100 in a Franz cell to simulate drug delivery into a body utilizing a pharmaceutical composition (also referred to as a therapeutic composition) that has positively-charged chemical species that are the ions of the active pharmaceutical ingredients (API) drug components to deliver. Franz cells are a widely used methodology to evaluate in vitro drug permeation, which have advantages, such as (i) accurate representative of the in vivo drug delivery which is an acceptable method to submit data to FDA, (ii) few handling of tissues, and (iii) low amount of drug required for analysis. Iontophoresis system 100 includes anode 101, the chamber 110 (containing the pharmaceutical composition 111), membrane 104 (such as cadaver human stratum corneum), cathode 102, control unit 103, receptor chamber 112 (with phosphate buffered saline), heater/circulator 113, water jacket 114, stir bar 115, and sampling port 116. For example, a jacketed 9 mm Franz cell with 5 mL receptor volume, flat ground joint, PermeGear part number #4G-01-00-09-05) (PermeGear, Inc., Hellertown, Pennsylvania) can be utilized in iontophoresis system 100 with a membrane 104 of a 25 mm×25 mm cadaver human stratum corneum. A coiled silver electrode is used in the donor side for the anode 101 electrode (such as to simulate the earset used in the Tula iontophoresis system (Tusker Medical, Menlo Park, California)).

Figure 2:
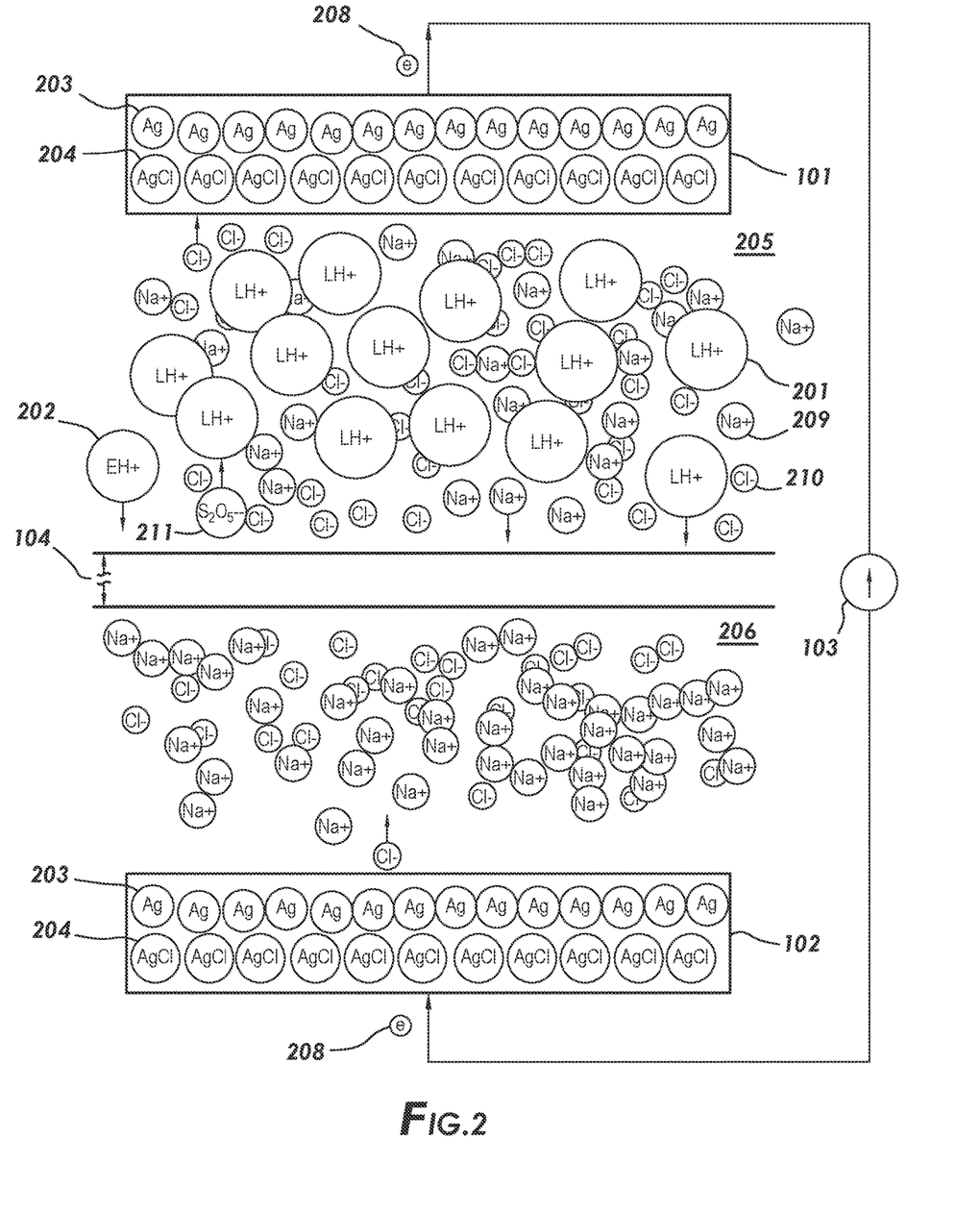
FIG. 2 is a schematic of the use of a prior art isotonic pharmaceutical composition in the iontophoresis system shown in FIG. 1.

FIG. 2 is a schematic showing a prior art isotonic pharmaceutical composition (that includes positive ions of the active ingredient (lidocaine ions ($LH^+$) 201 and epinephrine ions ($EH^+$) 202) in iontophoresis system 100. As seen in FIG. 2, the anode 101 is made of an electrode including silver (Ag) 203 and is positioned on the drug (or donor) side 205 of stratum corneum 104. During iontophoresis, silver chloride (AgCl) 204 is created on the electrode including silver 203 on anode 101. The cathode 102 includes Ag 203 and AgCl 204 and is positioned on the receptor side 206 (which simulates the human body) of stratum corneum 104.

Since isotonic drugs are injectable, the isotonic pharmaceutical composition 111 has a significant amount of sodium chloride (NaCl), which are non-active ingredients. Thus, pharmaceutical composition 111 includes other ions including sodium ions ($Na^+$) 209, chlorine ions ($Cl^-$) 210, and metabisulfite ions ($S_2O_5^{-2}$) 211. In the present circumstance shown in FIG. 2, The sodium ions 209 and the chlorine ions 210 are not all necessarily coming from the NaCl. For instance, the lidocaine ions 201 can come from the salt from lidocaine hydrochloride. Furthermore, for instance, sodium metabisulfite is a preservative for the epinephrine and cannot be removed from drug content (which creates a low amount of sodium ions 209 created and metabisulfite ions 211 low because the small amount of the sodium metabisulfite that is present).

In iontophoresis system 100, control unit 103 is used as the charger for the anode 101 and the cathode 102. Control unit 103 provides the small electric current (from an external generator), which permits the flow of electrons 208 from anode 101 to cathode 102. At anode 101, the electrons are generated as follows:

At cathode 102, the electrons are combined as follows:

When control unit 103 is providing the electric current, anode 101 is a positively-charged anode (which repeals the positively-charged chemical species, i.e., $LH^+$ 107, $EH^+$ 108, and $Na^+$ 109) and cathode 102 is a negatively-charged cathode (which attracts the positively-charged chemical species). This results in the positively-charged chemical species being driven through stratum corneum 104. By controlling the electric current of the control unit 103, this controls the driving of the positively-charged chemical species.

It should be noted that if the chemical species to be driven through stratum corneum 104 is a negatively-charged species, then the positions of the anode 101 and the cathode 102 in iontophoresis system 100 would need to be reversed, i.e., anode 101 would be on receptor side 106 and cathode 102 would be on drug side 105.

The TYMBION® brand drug (Tusker Medical, Menlo Park, California) is an example of a therapeutic composition that can be used for iontophoresis, such as the system shown in FIGS. 1-2. Tymbion drug is a lidocaine hydrochloride and epinephrine otic solution approved for the iontophoretic route of administration. Tymbion drug is a sterile, nonpyrogenic solution of lidocaine hydrochloride 2% (20 mg/mL) and epinephrine 1:100,000 (0.01 mg/mL) in water and is provided in 20 mL, single-patient-use vials. Inactive ingredients in the Tymbion drug are sodium chloride, sodium metabisulfite, citric acid, and methylparaben. The solution may contain hydrochloric acid to adjust pH. The control unit that can be used for the Tymbion drug is the control system of the Tula iontophoresis system (Tusker Medical).

Figure 3:
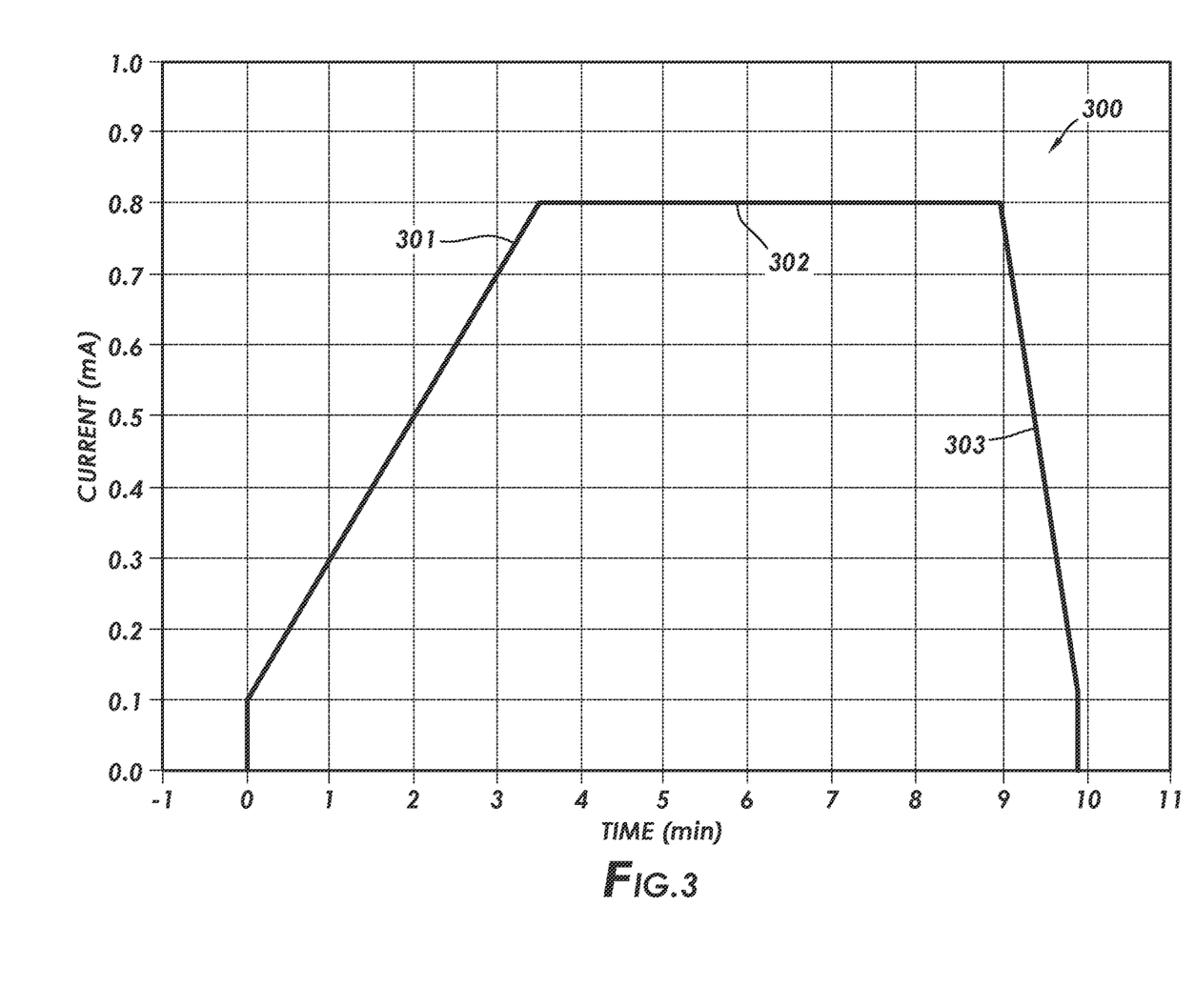
FIG. 3 is a graph showing a current profile that can provide a pre-determined measured dosage of the active ingredient of the prior art pharmaceutical composition shown in FIG. 2.

For instance, using the Tymbion drug and Tula iontophoresis system (from Tusker Medical), the iontophoresis system 100 can be utilized to provide a measured dosage of lidocaine and epinephrine. FIG. 3 shows a representative current profile 200 that can be used to provide such a predetermined measured dosage of the active ingredients of the Tymbion drug. The current profile has three sections, namely, a first section 301 in which the current of current profile 300 is ramped-up over a period of time. As shown in current profile 300, during the first section 301 (the "ramp-up period"), the current is ramped-up from 0.1 mA to 0.8 mA for a time period of about 3.5 minutes (beginning at time zero and ending at about time 3.5 minutes during the overall procedure time of current profile 300). This calculates to a "ramp-up rate" of around 3.33 µA/sec in current profile 300. The "ramp-up rate" is the change of current over the ramp-up time.

During the second section 302 (the "steady state period"), the current is maintained at the predetermined current ("steady state current") utilized for the treatment, which, in current profile 300, is a steady state current of 0.8 mA for a time period of about 5.5 minutes (beginning at about time 3.5 minutes and ending at about time 9 minutes during the overall procedure time of current profile 300).

During the third section 303 (the "ramp-down period"), the current is ramped-down from 0.8 mA at a rate of 12.3 µA/sec, which takes about 1 minute (beginning at about time 9 minutes ending at about time 10 minutes during the overall procedure time of current profile 300).

The sum of sections 301-303 yields an overall time period (the "application time") of current profile 300 of about 10 minutes.

Changing the profiles, such as by (a) reducing the overall treatment period (including each of the different sections), (b) reducing the current, and/or (c) accelerating the ramp-up rate, etc., while maintaining the measured dosage in the treatment would greatly benefit the patient. Accordingly, the need remains for improved pharmaceutical compositions for iontophoresis that maintain the same measured dosages treatments while easing the sensation upon the patient and increasing the efficiency of the system.

As used herein, "competing ions" are ions present in the pharmaceutical composition that are not ions of the active ingredient in the pharmaceutical composition but are ions that compete against the delivery of the ions of the active ingredient species.

The competing ions can have the same directional charge (positive or negative) as the charge of the ions of the active ingredient in the pharmaceutical composition. The magnitude of the charge of the competing ion can be the same or different from the ions of the active ingredient. I.e., the active ingredient ion could have a negative 2 charge (−2), while the same-directional competing ion could have a negative 1 (−1) charge. In such instance, the same-directional competing ions are attracted to and repulsed by the cathode and anode in the same direction as the active ingredient ions such that active ingredient ions and the non-active ingredient ions are both driven by the iontophoresis system in the same direction across the stratum corneum.

For example, when utilizing an iontophoresis system in which the isotonic pharmaceutical composition has ions of active ingredients that are positively-charged species (such as $LH^+$ or $EH^+$), $Na^+$ are same-directional competing ions. In such circumstance, the presence and concentration of $Na^+$ effects the driving of the active ingredients across the stratum corneum, as some of the current is utilize on the $Na^+$.

The competing ions can have the opposite directional charged ions as the charge of the ions of the active ingredient in the pharmaceutical composition. For example, $Cl^-$ are also a competing ion against delivery of the positively-charged species (such as $LH^+$ or $EH^+$). Therefore, removing the NaCl has the benefit of reducing both competing ions.

Likewise, when utilizing an iontophoresis system in which the isotonic pharmaceutical composition has ions of active ingredients that are negatively-charged species, $Na^+$ and $Cl^-$ are competing ions. In such circumstance, the presence and concentration of $Na^+$ and $Cl^-$ effects the driving of the active ingredients across the stratum corneum.

As for the profile of the application of current for a selected isotonic pharmaceutical composition (having an active ingredient that is positively or negatively charged ions in solution), the current profile has a ramp-up time, a steady state current, an application time, etc. to provide for the delivery of the pre-determined dosage utilizing iontophoresis. The terms "original ramp-up time," "original steady state current," "original application time," etc. shall be the ramp-up time, steady state current, and application time for the profile for applying electrical current used with the original selected pharmaceutical composition to deliver the pre-determined dosage utilizing iontophoresis.

Example embodiment comprise selecting an isotonic pharmaceutical composition (having an active ingredient that is positively or negatively charged ion) and then reducing/removing the competing ions from the pharmaceutical composition to form a modified pharmaceutical composition. In some embodiments, the competing ions are completely removed in the modified pharmaceutical composition. In other embodiments, a percentage of the competing ions are removed in the modified pharmaceutical composition, such as removing at least 50% molar concentration at least 75% molar concentration, or at least 90% molar concentration of the competing ions.

By removing/reducing the concentration of competing ions, the modified pharmaceutical composition can be used in the iontophoresis system to deliver the same pre-determined dosage using a modified profile. In some embodiments, for the modified profile: (a) the ramp-up time for the modified profile (the "modified ramp-up time") is 85% or less of the original ramp-up time, (b) the steady state current for the modified profile (the "modified steady state current") is 85% or less of the original steady state current, and (c) the application time for the modified profile (the "modified application time") is 75% or less of the original application time. Moreover, in some further embodiments, the ramp-up rate for the modified profile (the "modified ramp-up rate) can be 125% or more of the original ramp-up rate.

In some embodiments, for the modified profile (a) the modified ramp-up time is 80% or less of the original ramp-up time, (b) the modified steady state current is 80% or less of the original steady state current, and (c) the modified application time is 60% or less of the original current application time. Moreover, in some further embodiments, the ramp-up rate can be 150% or more of the original ramp-up rate.

In some embodiments, for the modified profile (a) the modified ramp-up time is 75% or less of the original ramp-up rate, (b) the modified steady state current is 75% or less of the original steady state current, and (c) the modified application time is 50% or less of the original application time. Moreover, in some further embodiments, the ramp-up rate can be 200% (i.e., double) or more of the original ramp-up rate.

Figure 4:
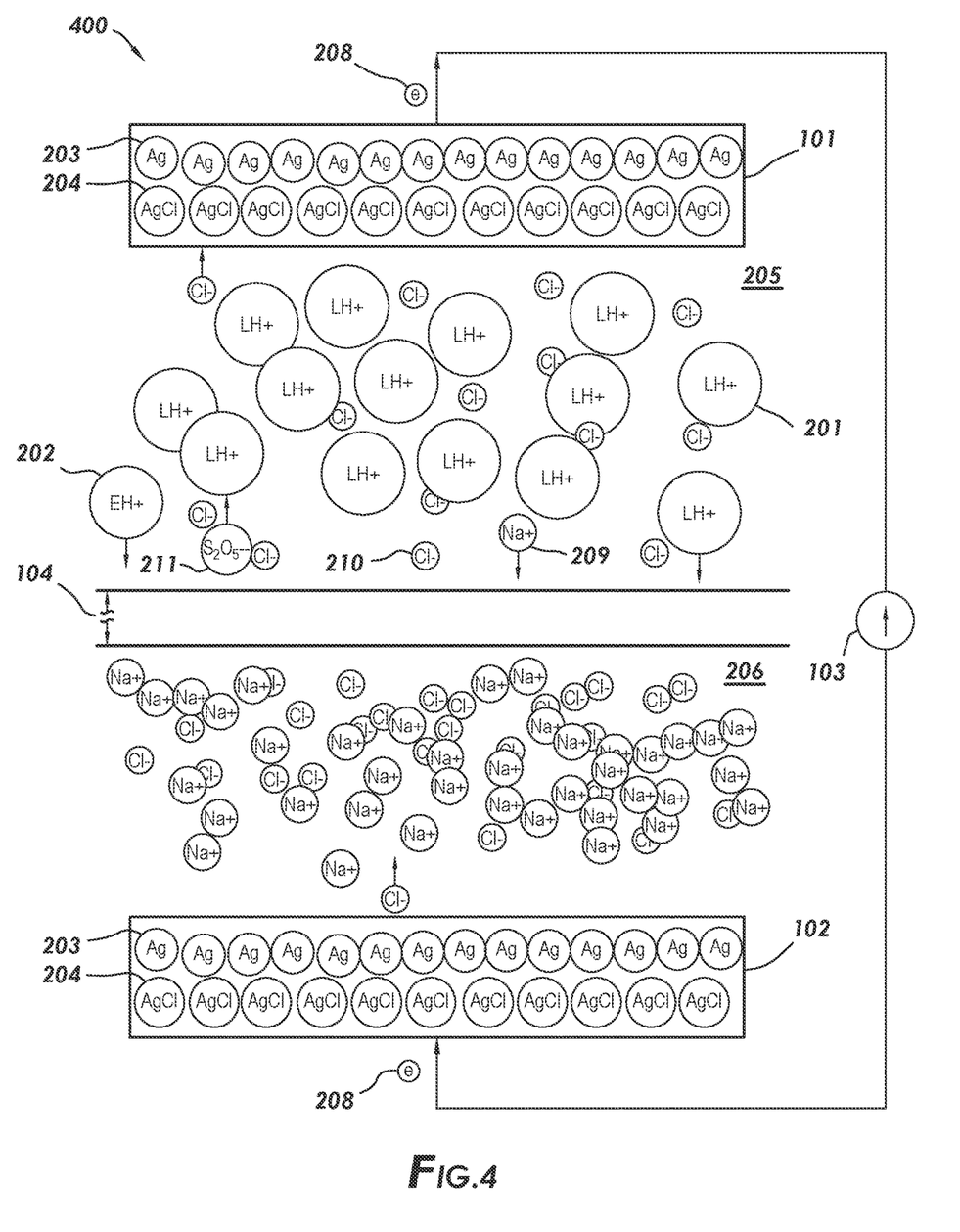
FIG. 4 is a schematic of a pharmaceutical composition modified in an embodiment in the iontophoresis system shown in FIG. 1.

For example, the Tymbion drug can be selected and nearly all of the Na+ and Cl− removed. This modified Tymbion drug can then be utilized in the example arrangement as shown in FIGS. 1-2. FIG. 4 shows the iontophoresis system of FIG. 1 with the Tymbion drug modified with nearly all of the Na+ 209 removed (so there are little to no Na+ ions on drug side 205) and Cl− 210 is reduced significantly. Note that all the Cl− ions cannot be removed because the lidocaine in the Tymbion drug is in the form of lidocaine hydrochloride.

Figure 5A:
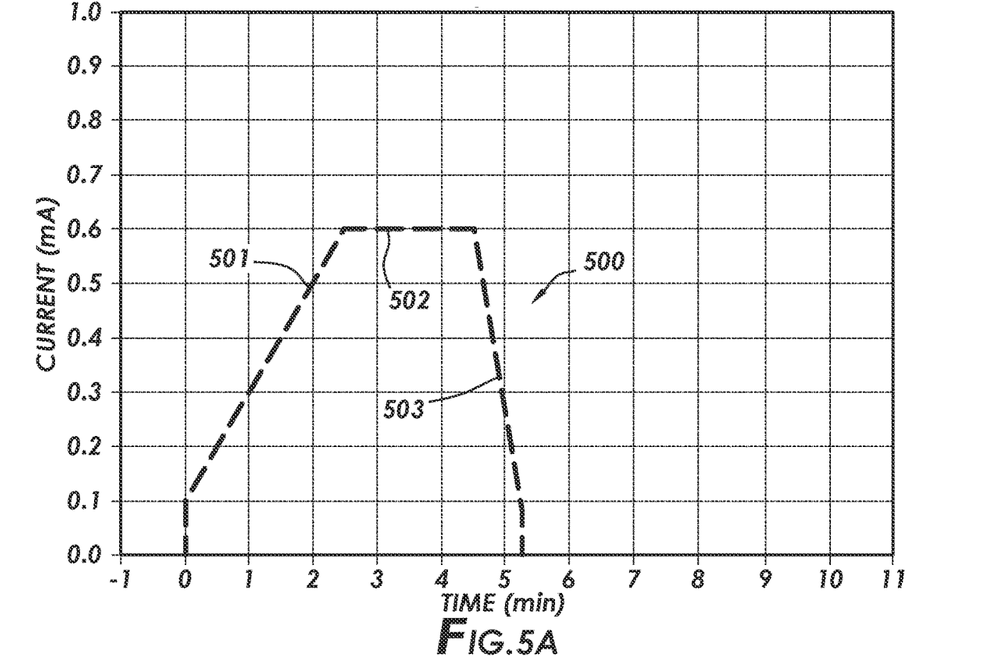
FIG. 5A is a graph showing a current profile that can provide the pre-determined measured dosage of the active ingredient of the modified pharmaceutical composition shown in FIG. 4.

FIG. 5A shows an example current profile 500 for the modified Tymbion drug, which provides for a similar pre-determined dosage of the active ingredients that was provided for the original Tymbion drug using current profile 300 shown in FIG. 3.

Current profile 500 has a first section 501, in which the current is ramped-up from 0.1 mA to 0.6 mA at a rate of 3.33 μA/sec for a period of about 2.5 minutes (beginning at time zero and ending at about time 2.50 minutes during the overall procedure time of current profile 500). While this is the same ramp-up rate shown in first section 301 of current profile 300, the ramp-up time has been decreased by a minute (2.5 minutes instead of 3.5 minutes), which is a less than 75% of the original ramp-up time. During the second section 502, the current is maintained at 0.6 mA for a time period of about 2.0 minutes (beginning at about time 2.5 minutes and ending at about time 4.5 minutes during the overall procedure time of current profile 500). This steady state current is about 75% of the steady state current shown in second section 302 of current profile 300. As compared to second section 302 of profile 300, the time of steady state current in second section 502 has decreased by about a minute (2 minutes instead of 3 minutes). During the third section 503, the current is ramped down very quickly (at a rate of 12.3 μA/sec for about 40 seconds) beginning at about time 4.5 minutes and ending at about 5.25 minutes. during the overall procedure time of current profile 500). As compared to second section 303 of profile 300, this is a reduction of time in the third section of about 20 seconds (40 seconds instead of one minute). Overall, the application time in current profile 500 is about 5.25 minutes to complete (which is less than about 60% of the application time in current profile 300).

Figure 5B:
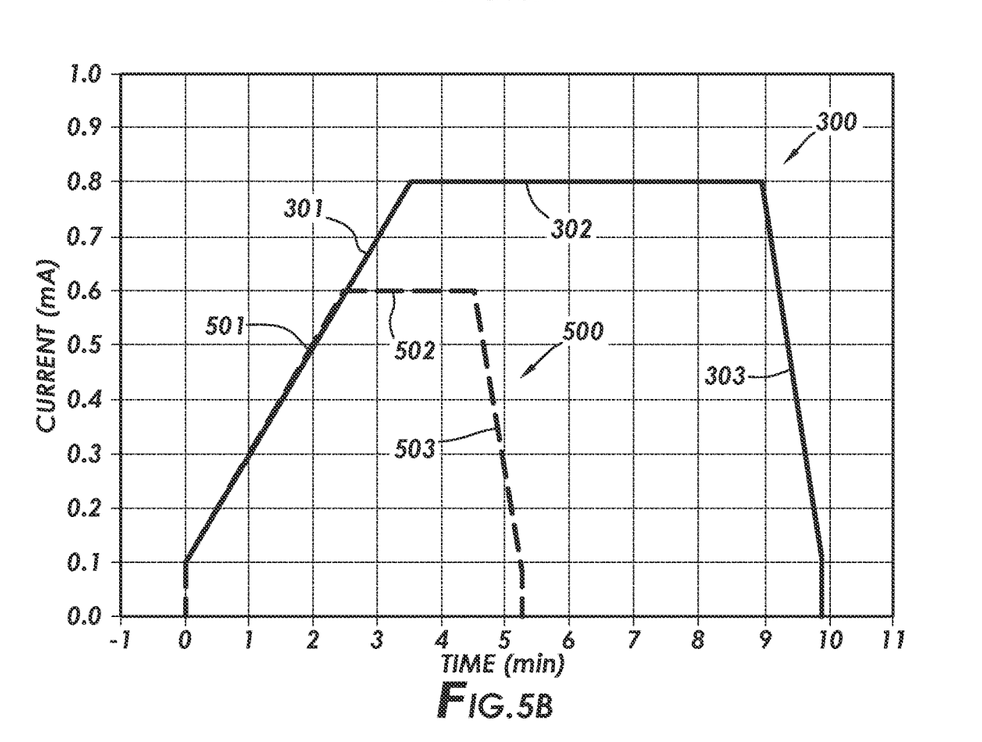
FIG. 5B is a graph showing a comparison of the current profiles of FIG. 3 and FIG. 5A.

A comparison of current profiles 300 and 500 is shown in FIG. 5B.

Figure 6A:
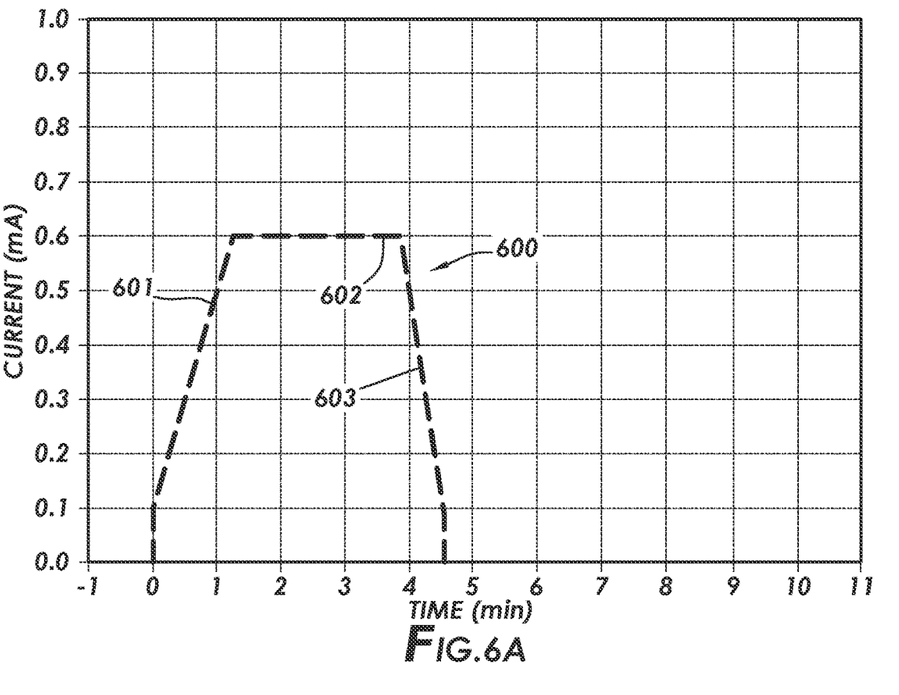
FIG. 6A is a graph showing an alternative current profile that can provide the pre-determined measured dosage of the active ingredient of the modified pharmaceutical composition shown in FIG. 4.

FIG. 6A shows an example current profile 600 for the modified Tymbion drug, which is different than current profile 500, and also provides for a similar pre-determined dosage of the active ingredients that was provided for the original Tymbion drug using current profile 300 shown in FIG. 3.

Current profile 600 has a first section 601, in which the current is ramped-up from 0.1 mA to 0.6 mA for a period of about 1.25 minutes (beginning at time zero and ending at about time 1.25 minutes during the overall procedure time of current profile 600). This calculates to a ramp-up rate of about 0.4 mA/min, which is about 200% of the ramp-up rate shown in first section 301 of current profile 300. During the second section 602, the current is maintained at 0.6 mA for a time period of about 2.75 minutes (beginning at about time 1.25 minutes and ending at about time 4 minutes during the overall procedure time of current profile 400). This steady state current is about 75% of the steady state current shown in second section 302 of current profile 300. During the third section 603, the current is ramped down very quickly (less than 30 seconds beginning at about time 4 minutes and ending at about time 4.5 minutes during the overall procedure time of current profile 600), so that the application time in current profile 600 is about 4.5 minutes to complete (which is less than about 50% of the application time in current profile 300).

Figure 6B:
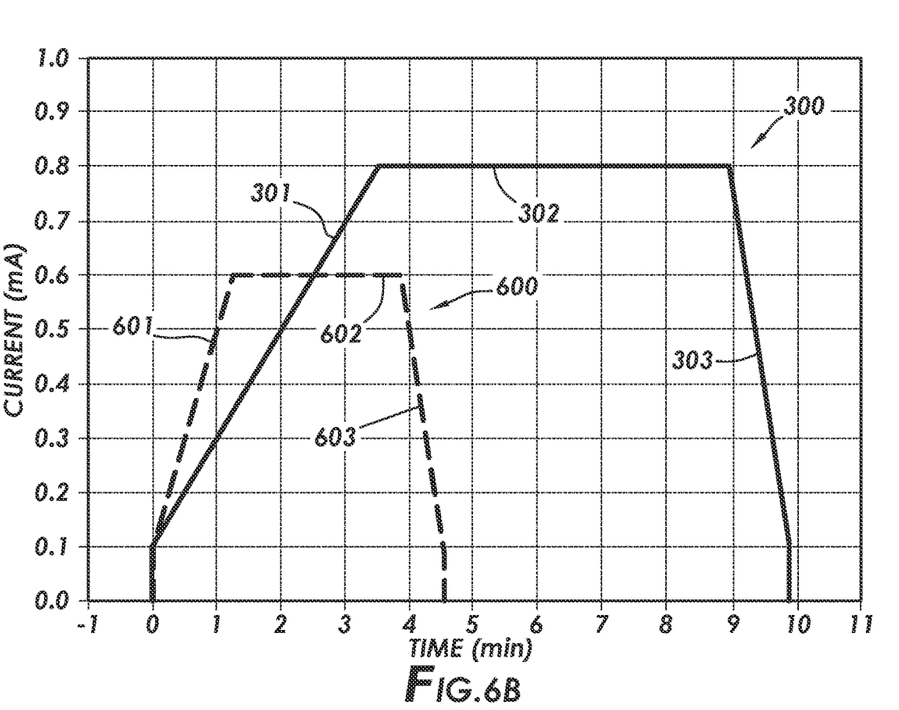
FIG. 6B is a graph showing a comparison of the current profiles of FIG. 3 and FIG. 6A.

A comparison of current profiles 300 and 600 is shown in FIG. 6B.

TABLE I shows a comparison of current profiles 300, 500, and 600 which shows current and general approximate times the current is applied.

TABLE I

|  | Profile 300 (Original Tymbion) | | Profile 500 (Modified Tymbion) | | Profile 600 (Modified Tymbion) | |
| --- | --- | --- | --- | --- | --- | --- |
|  | I(mA) | T(min) | I(mA) | T(min) | I(mA) | T(min) |
| Ramp-Up | 0.1 to 0.8 | 3.5 | 0.1 to 0.6 | 2.5 | 0.1 to 0.6 | 1.25 |
| Steady State | 0.8 | 5.5 | 0.6 | 2.0 | 0.6 | 2.75 |
| Ramp-Down | 0.8 to 0.1 | 1.0 | 0.6 to 0.1 | 0.75 | 0.6 to 0.1 | 0.5 |
| Total time |  | 10.0 |  | 5.25 |  | 4.5 |

As used herein, the term "measured pre-determined dosage" for a pharmaceutical composition is the dosage measured by utilizing the isontonic pharmaceutical composition in the Franz cell (iontophoresis system) as described and taught above for a specified profile. The term "standard measured pre-determined dosage" is the measure pre-determined dosage of the un-modified isotonic pharmaceutical composition in the Franz cell when applying the current profile 300. The term "revised measured pre-determine dosage" is the dosage obtained for the modified pharmaceutical composition in the same Franz cell using a specified profile, such as profiles 500 or 600.

Examples include those in which the revised measured pre-determine dosage of the modified pharmaceutical composition is the same or greater than the standard measured pre-determined dosage of the isontonic pharmaceutical composition.

For example, relative to a standard measured predetermined dosage of an isotonic pharmaceutical composition (which is a standard measured pre-determined dosage obtained when utilizing the isotonic pharmaceutical composition in a Franz cell performing iontophoresis using a standard profile of (i) a standard ramp-up from 0.1 mA to 0.8 mA for 3.5 minutes, (ii) a standard steady state at 0.8 mA for 5.5 minutes, and (iii) a standard ramp-down from 0.8 mA to 0.1 mA for 1 minute):

In some embodiments, the revised measured pre-determine dosage of the modified pharmaceutical composition (which is a revised measured pre-determine dosage obtained when utilizing the same Franz cell performing iontophoresis using a profile of (i) a ramp-up from 0.1 mA to 0.7 mA for 3 minutes, (ii) a steady state at 0.7 mA for 3.75 minutes, and (iii) a second ramp-down from 0.7 mA to 0.1 mA for 50 seconds) is the same or greater than the standard measured predetermined dosage.

In some embodiments, the revised measured pre-determine dosage of the modified pharmaceutical composition (which is a revised measured pre-determine dosage obtained when utilizing the same Franz cell performing iontophoresis using a profile of (i) a ramp-up from 0.1 mA to 0.6 mA for 2.5 minutes, (ii) a steady state at 0.6 mA for 2 minutes, and (iii) a second ramp-down from 0.7 mA to 0.1 mA for 40 seconds) is the same or greater than the standard measured predetermined dosage.

In some embodiments, the revised measured pre-determine dosage of the modified pharmaceutical composition (which is a revised measured pre-determine dosage obtained when utilizing the same Franz cell performing iontophoresis using a profile of (i) a ramp-up from 0.1 mA to 0.6 mA for 1.25 minutes, (ii) a steady state at 0.6 mA for 2.75 minutes, and (iii) a second ramp-down from 0.7 mA to 0.1 mA for 30 seconds) is the same or greater than the standard measured predetermined dosage.

It should be noted that the comparison between the isotonic pharmaceutical composition and the modified pharmaceutical composition with respect to the standard measured pre-determined dosage and the revised measured pre-determined dosage is to provide measurable characteristics of the modified pharmaceutical composition. However, the modified pharmaceutical composition can then be used for iontophoresis with any profile tailored to the particular patient and the patient's needs. Such profile will be provide that during the step of performing iontophoresis with iontophoresis with the revised pharmaceutical composition for a pre-determined dosage, the overall time and maximum current will be reduced, as compared to performing iontophoresis with the isotonic pharmaceutical composition to provide the pre-determined dosage.

One possible advantage of the example embodiments is that the method takes existing isotonic drugs and then modifies them by removing non-active ingredients (namely the competing ions, such as $Na^+$ and $Cl^-$) instead of having to develop a new drug from scratch. By such modification, the modified pharmaceutical composition (with reduced/removed competing ions) results in a reduced maximum current and a shorter overall procedure (including a quicker ramp-up period due to an increased ramp-up rate and the reduced maximum current), as compared to the original isotonic drug, which is beneficial to the patient, particularly on a sensation perspective.

Furthermore, by ramping-up more quickly, the active ingredients can begin work more quickly. For instance, in the case of active ingredients lidocaine and epinephrine, this more rapidly anesthetizes the patient, which further lessens discomfort for the patient.

By reducing/removing the competing ions, it also renders the iontophoresis more efficient, as the applied current (which again is much lower) is being directed to driving the active ingredients of the pharmaceutical composition, instead of also the non-active ingredients (which ions having the same direction charge).

While embodiments of the invention have been shown and described, modifications thereof can be made by one skilled in the art without departing from the spirit and teachings of the invention. The embodiments described and the examples provided herein are exemplary only and are not intended to be limiting. Many variations and modifications of the invention disclosed herein are possible and are within the scope of the invention. The scope of protection is not limited by the description set out above, but is only limited by the claims which follow, that scope including all equivalents of the subject matter of the claims.

The disclosures of all patents, patent applications, and publications cited herein are hereby incorporated herein by reference in their entirety, to the extent that they provide exemplary, procedural, or other details supplementary to those set forth herein.

Amounts and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of approximately 1 to approximately 4.5 should be interpreted to include not only the explicitly recited limits of 1 to approximately 4.5, but also to include individual numerals such as 2, 3, 4, and sub-ranges such as 1 to 3, 2 to 4, etc. The same principle applies to ranges reciting only one numerical value, such as "less than approximately 4.5," which should be interpreted to include all of the above-recited values and ranges. Further, such an interpretation should apply regardless of the breadth of the range or the characteristic being described.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a" and "an" mean "one or more" when used in this application, including the claims.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that can vary depending upon the desired properties sought to be obtained by the presently disclosed subject matter.

As used herein, the term "about" and "substantially" when referring to a value or to an amount of mass, weight, time, volume, concentration or percentage is meant to encompass variations of the following: in some embodiments ±20%, in some embodiments ±10%, in some embodiments ±5%, in some embodiments ±1%, in some embodiments ±0.5%, and in some embodiments ±0.1%, each with respect to or from the specified amount, as such variations are appropriate to perform the disclosed method.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

What is claimed is:

1. A method comprising:
   (a) selecting an isotonic pharmaceutical composition comprising
      (i) charged ions of one or more active ingredients, and
      (ii) competing ions of one or more non-active ingredients, wherein the isotonic pharmaceutical composition is operable for being used in an iontophoresis system to perform iontophoresis;
   (b) removing at least 50% molar concentration of the competing ions from the isotonic pharmaceutical composition to produce a revised pharmaceutical composition; and (c) utilizing the revised pharmaceutical composition in the iontophoresis system to perform iontophoresis.

2. The method of claim 1, wherein the charged ions of the one or more active ingredients are positively charged ions.

3. The method of claim 1, wherein the charged ions of the one or more active ingredients are negatively charged ions.

4. The method of claim 1, wherein
(a) the one or more active ingredients comprise (i) lidocaine, (ii) epinephrine, or (iii) a combination of both; and
(b) the competing ions of the one or more non-active ingredients comprise (i) sodium ions, (ii) chlorine ions, or (iii) a combination of both.

5. The method of claim 1, wherein at least 75% molar concentration of the competing ions of the one or more non-active ingredients are removed from the isotonic pharmaceutical composition to produce the revised pharmaceutical composition.

6. The method of claim 1, wherein at least 90% molar concentration of the competing ions of the one or more non-active ingredients are removed from the isotonic pharmaceutical composition to produce the revised pharmaceutical composition.

7. The method of claim 1, wherein all of the competing ions are removed from the isotonic pharmaceutical composition to produce the revised pharmaceutical composition.

8. The method of claim 1, wherein
(a) the isotonic pharmaceutical composition has a standard measured pre-determined dosage characteristic;
(b) the revised pharmaceutical composition has a revised measured pre-determined dosage characteristic;
(c) the standard measured pre-determined dosage characteristic is a standard measured pre-determined dosage obtained when utilizing the isotonic pharmaceutical composition in a Franz cell performing iontophoresis using a standard profile of (i) a standard ramp-up from 0.1 mA to 0.8 mA for 3.5 minutes, (ii) a standard steady state at 0.8 mA for 5.5 minutes, and (iii) a standard ramp-down from 0.8 mA to 0.1 mA for 1 minute;
(d) the revised measured pre-determined dosage characteristic is a revised measured pre-determined dosage obtained when utilizing the revised pharmaceutical composition in the Franz cell performing iontophoresis using a second profile of (i) a second ramp-up from 0.1 mA to 0.7 mA for 3 minutes, (ii) a second steady state at 0.7 mA for 3.75 minutes, and (iii) a second ramp-down from 0.7 mA to 0.1 mA for 50 seconds; and
(e) the revised measured pre-determined dosage is equal or greater than the standard measured pre-determined dosage.

9. The method of claim 8, wherein
(a) the one or more active ingredients comprise (i) lidocaine, (ii) epinephrine, or (iii) a combination of both; and
(b) the competing ions of the one or more non-active ingredients comprise (i) sodium ions, (ii) chlorine ions, or (iii) a combination of both.

10. The method of claim 8, wherein at least 75% molar concentration of the competing ions of the one or more non-active ingredients are removed from the isotonic pharmaceutical composition to produce the revised pharmaceutical composition.

11. The method of claim 8, wherein at least 90% molar concentration of the competing ions of the one or more non-active ingredients are removed from the isotonic pharmaceutical composition to produce the revised pharmaceutical composition.

12. The method of claim 8, wherein all of the competing ions of the one or more non-active ingredients are removed from the isotonic pharmaceutical composition to produce the revised pharmaceutical composition.

13. The method of claim 1, wherein
(a) at least 75% molar concentration of the competing ions of the one or more non-active ingredients are removed from the isotonic pharmaceutical composition to produce the revised pharmaceutical composition;
(b) the isotonic pharmaceutical composition has a standard measured pre-determined dosage characteristic;
(c) the revised pharmaceutical composition has a revised measured pre-determined dosage characteristic;
(d) the standard measured pre-determined dosage characteristic is a standard measured pre-determined dosage obtained when utilizing the isotonic pharmaceutical composition in a Franz cell performing iontophoresis using a standard profile of (i) a standard ramp-up from 0.1 mA to 0.8 mA for 3.5 minutes, (ii) a standard steady state at 0.8 mA for 5.5 minutes, and (iii) a standard ramp-down from 0.8 mA to 0.1 mA for 1 minute;
(e) the revised measured pre-determined dosage characteristic is a revised measured pre-determined dosage obtained when utilizing the revised pharmaceutical composition in the Franz cell performing iontophoresis using a second profile of (i) a second ramp-up from 0.1 mA to 0.6 mA for 2.5 minutes, (ii) a second steady state at 0.6 mA for 2 minutes, and (iii) a second ramp-down from 0.6 mA to 0.1 mA for 40 seconds; and
(e) the revised measured pre-determined dosage is equal or greater than the standard measured pre-determined dosage.

14. The method of claim 13, wherein
(a) the one or more active ingredients comprise (i) lidocaine, (ii) epinephrine, or (iii) a combination of both; and
(b) the competing ions of the non-active ingredient comprise (i) sodium ions, (ii) chlorine ions, or (iii) a combination of both.

15. The method of claim 13, wherein at least 90% molar concentration of the competing ions of the one or more non-active ingredients are removed from the isotonic pharmaceutical composition to produce the revised pharmaceutical composition.

16. The method of claim 15, wherein
(a) the one or more active ingredients comprise (i) lidocaine, (ii) epinephrine, or (iii) a combination of both; and
(b) the competing ions of the one or more non-active ingredients comprise (i) sodium ions, (ii) chlorine ions, or (iii) a combination of both.

17. The method of claim 13, wherein all of the competing ions of the one or more non-active ingredients are removed from the isotonic pharmaceutical composition to produce the revised pharmaceutical composition.

18. The method of claim 1, wherein
(a) at least 75% molar concentration of the competing ions of the one or more non-active ingredients are removed from the isotonic pharmaceutical composition to produce the revised pharmaceutical composition;
(b) the isotonic pharmaceutical composition has a standard measured pre-determined dosage characteristic;
(c) the revised pharmaceutical composition has a revised measured pre-determined dosage characteristic;
(d) the standard measured pre-determined dosage characteristic is a standard measured pre-determined dosage obtained when utilizing the isotonic pharmaceutical composition in a Franz cell performing iontophoresis using a standard profile of (i) a standard ramp-up from 0.1 mA to 0.8 mA for 3.5 minutes, (ii) a standard steady state at 0.8 mA for 5.5 minutes, and (iii) a standard ramp-down from 0.8 mA to 0.1 mA for 1 minute;

(e) the revised measured pre-determined dosage characteristic is a revised measured pre-determined dosage obtained when utilizing the revised pharmaceutical composition in the Franz cell performing iontophoresis using a second profile of (i) a second ramp-up from 0.1 mA to 0.6 mA for 1.25 minutes, (ii) a second steady state at 0.6 mA for 2.75 minutes, and (iii) a second ramp-down from 0.6 mA to 0.1 mA for 30 seconds; and (f) the revised measured pre-determined dosage is equal or greater than the standard measured pre-determined dosage.

19. The method of claim 18, wherein
(a) the one or more active ingredients comprise (i) lidocaine, (ii) epinephrine, or (iii) a combination of both; and
(b) the competing ions of the one or more non-active ingredients comprise (i) sodium ions, (ii) chlorine ions, or a combination of both.

20. The method of claim 18, wherein at least 90% molar concentration of the competing ions are removed from the isotonic pharmaceutical composition to produce the revised pharmaceutical composition.

21. The method of claim 20, wherein
(a) the one or more active ingredients comprise (i) lidocaine, (ii) epinephrine, or (iii) a combination of both; and
(b) the competing ions of the one or more non-active ingredients comprise (i) sodium ions, (ii) chlorine ions, or (iii) a combination of both.

22. The method of claim 18, wherein all of the competing ions of the non-active ingredients are removed from the isotonic pharmaceutical composition to produce the revised pharmaceutical composition.

23. The method of claim 1, wherein, during the step of performing iontophoresis with the revised pharmaceutical composition for a pre-determined dosage, overall time and maximum current are reduced, as compared to performing iontophoresis with the isotonic pharmaceutical composition to provide the pre-determined dosage.

24. The method of claim 23, wherein the charged ions of the one or more active ingredients are positively charged ions.

25. The method of claim 23, wherein the charged ions of the one or more active ingredients are negatively charged ions.

26. The method of claim 23, wherein
(a) the one or more active ingredients comprise (i) lidocaine, (ii) epinephrine, or (iii) a combination of both; and
(b) the competing ions of the one or more non-active ingredients comprise (i) sodium ions, (ii) chlorine ions, or (iii) a combination of both.

27. The method of claim 23, wherein at least 75% molar concentration of the competing ions of the one or more non-active ingredients are removed from the isotonic pharmaceutical composition to produce the revised pharmaceutical composition.

28. The method of claim 23, wherein at least 90% molar concentration of the competing ions of the one or more non-active ingredients are removed from the isotonic pharmaceutical composition to produce the revised pharmaceutical composition.

29. The method of claim 23, wherein all of the competing ions of the one or more non-active ingredients are removed from the isotonic pharmaceutical composition to produce the revised pharmaceutical composition.

* * * * *